United States Patent [19]

Jermyn

[11] Patent Number: 4,964,663
[45] Date of Patent: Oct. 23, 1990

[54] DEVICE FOR HANDLING A PLASTIC CONTACT LENS

[76] Inventor: Arthur C. Jermyn, 15914 Overview Rd., Poway, Calif. 92064

[21] Appl. No.: 425,487

[22] Filed: Oct. 23, 1989

[51] Int. Cl.$^5$ ............................................. A47F 9/00
[52] U.S. Cl. .................................... 294/1.2; 294/99.2
[58] Field of Search ...................... 294/1.2, 99.2, 902; 351/160 R; 606/1, 210

[56] References Cited

U.S. PATENT DOCUMENTS

| | | | |
|---|---|---|---|
| 3,317,989 | 5/1967 | Cull | 294/99.2 X |
| 3,818,784 | 6/1974 | McClure | 294/99.2 |
| 4,245,859 | 1/1981 | Rainin | 294/99.2 X |
| 4,457,756 | 7/1984 | Kern et al. | 606/210 X |
| 4,479,672 | 10/1984 | Jermyn | 294/1.2 |
| 4,750,771 | 6/1988 | Emmett et al. | 294/99.2 |

Primary Examiner—Margaret A. Focarino
Assistant Examiner—Dean J. Kramer
Attorney, Agent, or Firm—Lloyd F. Seebach

[57] ABSTRACT

The invention relates to a device for handling a plastic lens to remove the same from an eye of a user. The device is of a tweezer or pincer type comprising two arms that are joined at one end to form a unit with the arms at an acute angle and having a common plane in which the arms can be moved one toward the other. Each arm is provided at its free end with an extension angularly disposed relative to its respective arm and to the plane of movement. A soft holder of generally ellipsoidal shape and having axially arranged peripheral slots is mounted on each extension. The angular relationship between the arms and the extensions and holders permits the device to be accurately aligned with the lens in place over the eye without obstructing the user's vision as the device is moved toward the eye for engagement of the lens within its peripheral edge by the holders. The contact lens is positively engaged within its peripheral edge by the slots in each holder and is folded as the arms are moved into a position of minimum seraration in which position the plastic lens has been effectively released from the eye for complete removal by the device.

3 Claims, 2 Drawing Sheets

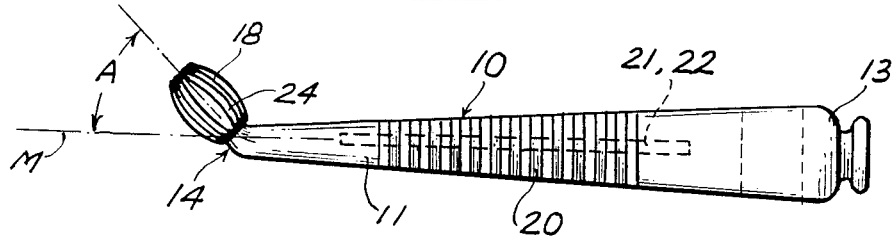
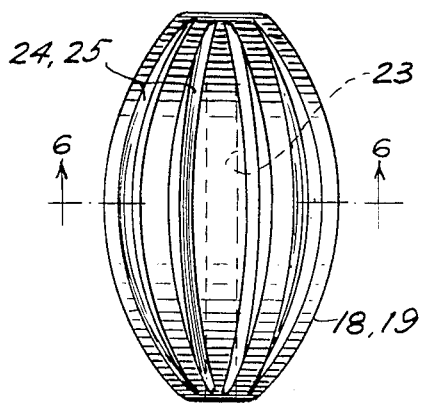
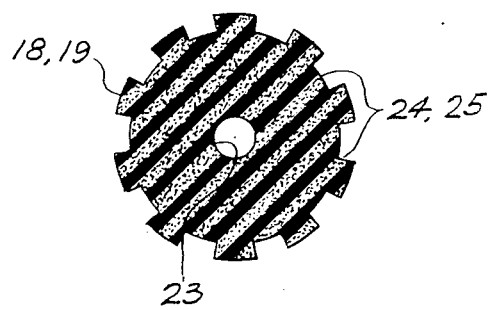
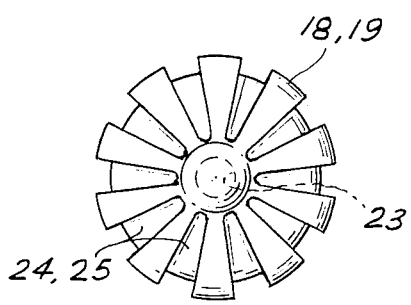

DEVICE FOR HANDLING A PLASTIC CONTACT LENS

FIELD OF THE INVENTION

The invention relates to a device for handling contact lenses and more particularly to a device for engaging and removing a plastic contact lens already in position relative to the eye of a user.

DESCRIPTION OF THE ART

It is common practice to remove a contact lens whether of the smaller more rigid type or the larger or so-called "soft type" lens from the cornea of an eye with fingers. This practice is difficult to accomplish with any ease, accuracy or safety. In the event a mirror is used, wetted fingers are usually of such breadth that they block most, if not all, of the mirror image of the eye so the mirror, in effect, is useless when it is really needed most, that is, when the finger(s) is in very close proximity to the eye.

Applicators of various types are available for applying or positioning a contact lens relative to the eye of a user but as such as not capable of removing the lens once it has been positioned relative to the eye. In most instances, the contact lens is first gripped about its peripheral edge or flange in such a manner that the user can peer or look through the lens as it is brought into position with respect to the eye for placement thereover. With respect to such applicators, release of the lens when it is very close to the eye presents a problem. In some cases, this problem is circumvented by placing the contact lens on or within a ring, but this does not alleviate the problem because the lens cannot be easily released from the applicator. Such an applicator is disclosed in U.S. Pat. No. 3,132,887.

A "soft" contact lens is made of a hydrophillic material which, when hydrated, is extremely pliable and requires special cleaning, storage, removal and insertion techniques. As an example of the unusual characteristics of the "soft" contact lenses, the same must be slightly folded or distorted to remove it from the wearer's eye and must be thoroughly aseptisized, preferably by special equipment. Because of these features of the "soft" contact lens, handling of the same by the user's fingers often result in injury to both the eye and to the lens from fingernails, rough hands and the like. Also, oil, dirt and other foreign matter from the user's hands can easily damage the lens and/or cause injury to the eye. The disclosure in U.S. Pat. No. 4,126,345 discloses a resilient pincer-arms type of device in which one end of the device is used for positioning the lens relative to the eye and the other is used for removing the lens from the eye. In no way does this disclosure alleviate the problem of unobstructed vision of the user when the device is used for removal of the plastic contact lens from the eye.

Other prior art in this field, such as, U.S. Pat. Nos. 3,879,076, 4,082,339 and 4,167,283 relate to handling a plastic contact lens for either applying the lens to the eye or removing the lens from the eye. Such devices do not disclose a structure capable of performing the act of removing the contact lens as efficiently or easily as the device disclosed and described hereinafter.

In my U.S. Pat. No 4,479,672 there is disclosed a device for handling a "soft" contact lens. This device is in the form of an inserter on which the lens is held by a viscous material for positioning the lens relative to the eye with a minimum of effort and with ease of release of the lens from the inserter. While this disclosure is readily adaptable to the positioning of the lens relative to the eye, it has certain drawbacks with respect to removing the lens from the eye. For this reason, it became apparent that a device such as disclosed herein, fulfills a need for a device which can easily engage and remove the lens in an efficient and safe manner.

SUMMARY OF THE INVENTION

It is an object of the invention to provide a device for engaging and removing a soft plastic contact lens in position relative to the eye of a user by which the contact lens is engaged within its peripheral edge and folded to release the contact lens from the eye in an efficient and easy manner.

Another object of the invention is to provide a device for engaging and removing a soft plastic contact lens in position relative to the eye of a user which can be moved toward the eye to position the device relative to the lens for engaging and removing the same from the eye without obscuring the vision of the user.

Still another object of the invention is to provide a device for engaging and removing a soft plastic contact lens in position relative to the eye of a user and which is provided with spaced holders for the lens arranged at an angle relative to the plane of movement of the arms forming the device so that the fingers of the user manipulating the device do not obstruct the user's vision as the device is moved toward the eye to engage the surface of the contact lens for removal thereof from the eye.

Yet another object of the invention is to provide a device for engaging and removing a soft plastic contact lens in position relative to the eye of a user which is of a pincer type having a holder on each pincer arm for engaging the lens within its diameter and arranged at an angle to the plane of movement of the arms so as not to obstruct the vision of the user as the device is moved toward the eye for engaging the lens and folding the same when the arms are moved one toward the other to effect removal of the lens from the eye.

These and other objects and advantages of the invention will be apparent to those skilled in the art by the description which follows and which is made in conjunction with the accompanying drawings.

Briefly, the objects of the invention are attained by utilizing a device comprising a first arm and a second arm which are resiliently connected or joined at one end to provide a unitary structure for establishing a position of maximum separation of the free ends of the arms and which are movable one toward the other in the same plane into a position of minimum separation of the free ends of the arms. Each arm is provided with an extension which is integral and coextensive with the free end of its respective arm and angularly arranged relative to its respective arm as well as to the plane of movement of the arms. A contact lens holder having spaced peripheral slots or grooves is mounted on each extension for releasibly engaging the lens within its peripheral edge or diameter and slightly folding the same as the arms are moved from the position of maximum separation toward that of minimum separation. With this arrangement, the contact lens is first engaged by the holders, then grasped by the edges of the slot(s) on each holder and folded as the arms are moved into the position of minimum separation for first releasing the lens from the eye and then ultimately removing the lens.

Initially, the device is moved toward the eye with the arms in the position of maximum separation. In this position, the device could be moved toward the eye without obscuring the vision of the user. Since each extension and, hence, the holder thereon is arranged at an angle to the arm, the fingers holding the device are not in a position to block or obstruct the user's vision and, hence, are not aligned in any way with the eye nor the lens in position thereover. In such a relationship between the arms and the lens holders, the fingers of the user are completely out of sight so the user sees only the space between the separated lens holders as the device is moved toward the eye for positioning the device relative to the lens for removal of the same.

The lens holder mounted on each extension is molded of a very soft plastic material and is provided with axial slots or grooves so the contact lens can be readily engaged or grasped when the holders are positioned thereon and within the periphery thereof. The holder on each extension tip is ellipsoidal in shape and this shape together with the slots and the angular relationship thereof to the plane of movement of the arms of the device permits the angle at which the device is held by the user to vary without causing any harm or irritation of the cornea as the device is positioned with respect to the eye for removal of the contact lens therefrom. It can be appreciated that the ellipsoidal shape of the lens holders together with the slots in the periphery of the holders and the angular relation of the holders to the arms of the device, in effect, permits the contact lens to be easily engaged or grasped irrespective of any small angular changes in the relation of the device to the face or the eye of the user.

DESCRIPTION OF THE DRAWINGS

Reference is now made to the accompanying drawings wherein like reference numerals designate like parts and wherein:

FIG. 4 is a side elevational view of the device, as shown in FIG. 3;

FIG. 5 is an enlarged elevational view of a holder showing the generally ellipsoidal shape and the grooves in the periphery of the holder which extend axially thereof;

FIG. 6 is a sectional view taken along the line 6—6, as shown in FIG. 5; and

FIG. 7 is a top plan view of the holder, as seen in FIG. 5.

DESCRIPTION OF PREFERRED EMBODIMENTS OF THE INVENTION

Figure 1:
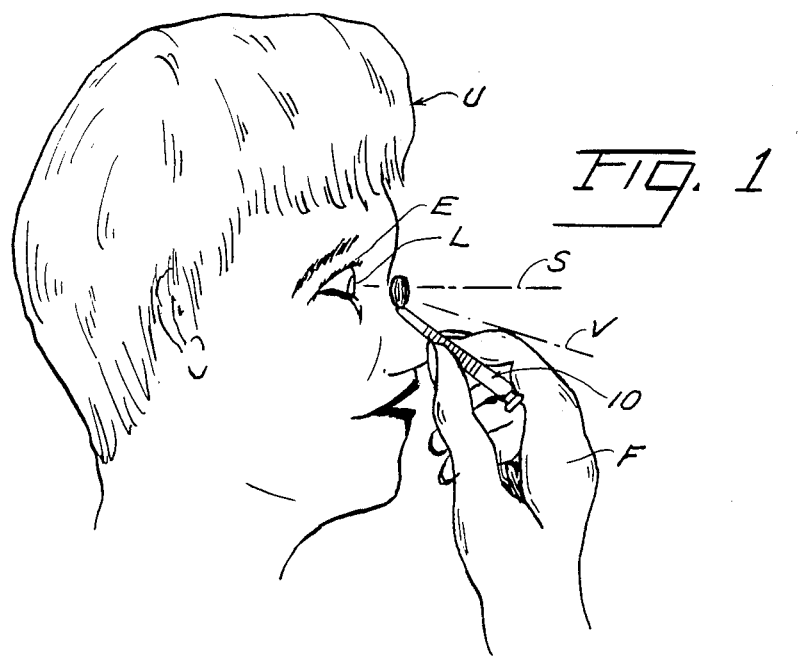
FIG. 1 is a profile or side view of the face of a user showing the manner in which the device is held for movement of the device toward the eye with the fingers of the user in a position in which the vision of the user is not obscured.
Figure 2:
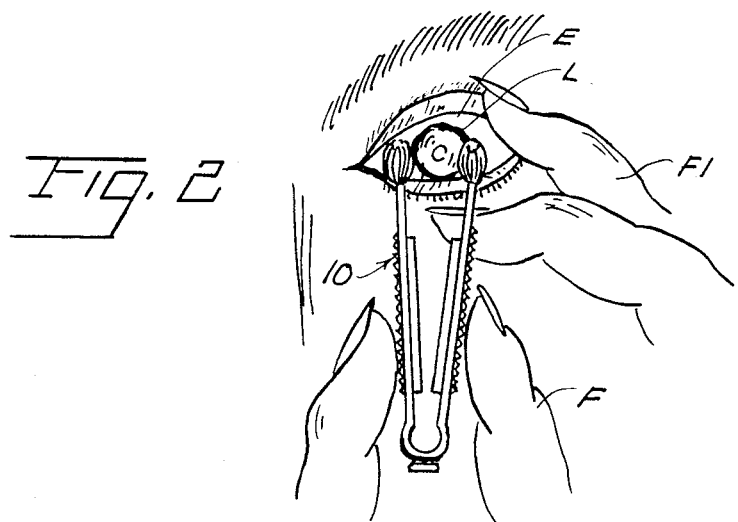
FIG. 2 is a partial front view of the eye of a user showing the position of the device relative to the eye and the contact lens thereover for use in engaging and removing a soft plastic contact lens from the eye of a user wherein the line of vision of the user is not obscured.

With reference to FIG. 1 and FIG. 2, a device 10 in accordance with the invention is shown as being held by a user U for engaging and removing a soft plastic contact lens L in position relative to the eye E of the user. It should be noted that the line of sight, as indicated by the line S, is in no way obstructed by the fingers F of the user holding the device nor by the device per se. In FIG. 1, the fingers F lie well below the field of vision as indicated by the line B. As shown in FIG. 2, the lids of the eye E can be extended by the fingers F1 of the other hand, if needed, to make the removal of the lens easier by providing more access to the lens per se.

The device 10 comprises three essential parts, namely: a first arm 11, a second arm 12 and a section 13 which joins the arms 11 and 12 at one end thereof to effectively form a single unit. This same structure can be attained in other ways with the use of different materials providing the same requisites. The free end 14 of arm 11 and the free end 15 of arm 12 are each provided with a respective extension 16 and 17 on each of which a soft plastic holding member 18 and 19 is respectively mounted.

The arms 11 and 12 together with the joining section 13 are molded, preferably, from a hard, resilient polypropylene plastic material so as to give a relative stiffness to the arms 11 and 12 and, at the same time, to fix the separation D between the innermost portions of the holders on the tips 18 and 19 on the extension 16 and 17 when not in use. The outer surfaces of the arms 11 and 12 can be provided with serrations 20 to provide easier and more positive manipulation of the device 10. As noted in FIG. 3, the device 10 comprises, in effect, a pincer which permits the arms 11 and 12 to be moved toward one another in the same plane M for gripping or engaging the surface of the soft plastic contact lens L within its peripheral edge. As shown in FIG. 4, the extensions 16 and 17, and hence, the holders 18 and 19, are arranged at an angle A to the plane of movement M of their respective arms 11 and 12 for a reason set forth hereinafter.

Figure 3:
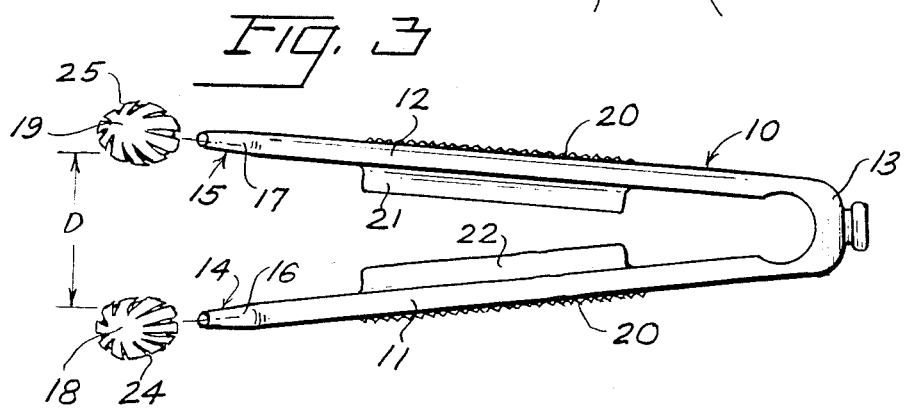
FIG. 3 is an elevational view of the device as contemplated for use in engaging and removing a soft plastic contact lens from the eye of a user.

The relationship between the innermost portions of the holders 18 and 19, as indicated by D in FIG. 3, can be described as the position of maximum separation of the arms 11 and 12 which is slightly less than the normal diameter of most soft, plastic lenses. Movement of the arms 11 and 12 toward one another in the same plane M is limited by engagement of the lugs 21 and 22 on the facing surfaces of the respective arms 11 and 12, thereby establishing a position of minimum separation of the innermost portions of the holders 18 and 19. The lengths of the lugs 21 and 22 must be such that when the arms 11 and 12 are moved toward one another and into the position of minimum separation, the lugs 21 and 22 are in engagement and no further override of the holders 18 and 19 can be accomplished due to pivotal action of the arms. This is essential to eliminate damage to the contact lens L when it is folded to release it from the eye for removal therefrom by the device 10.

With reference to FIG. 5, the holders 18 and 19 which are positioned on the respective extensions 16 and 17 are generally ellipsoidal in shape and each holder is provided with a blind central aperture 23 for receiving the extension on one of the arms. Each of holders 18 and 19 is provided with a plurality of peripherally spaced, axial slots or grooves 24 and 25, respectively, as seen in FIGS. 5, 6 and 7. With a plurality of such grooves 24 and 25, it is not necessary that the holder be positioned on its respective extension 16 and 17 in a particular way or manner. The surface within the peripheral edge of the plastic lens L will be engaged by a facing groove on each holder. Also, the facing groove on each holder will engage the surface of the lens L within the peripheral edge even if the lens is not located centrally of the holder but toward one end or the other of the holder In order words, the device 10 can hold or pick up the contact lens L even though the holders 18 and 19 are not properly oriented relative to the lens at precisely the required angle, this factor being due to the shape of the holder in conjunction with the grooves. Hence, there is no need for an exacting position of the holders relative to the surface of the eye or the lens for engaging the latter prior to removal. So long as some part of the facing grooves 24, 25 on the holders can diametrically engage the lens within its peripheral edge, the lens will be held or grasped in such a manner as to be readily removed from the eye.

It should also be noted that since the minimum separation position as determined by holders 18 and 19 in conjunction with the lugs 21 and 22, is less than the diameter of the soft, plastic lens L, the lens will be distorted or folded so as to secure its position between the holders. Although this distortion or folding is necessary to insure complete grasping of the lens by the opposed grooves of the holders, it in no way harms or causes the lens to assume some shape other than that originally intended.

With respect to the device 10, it has been found that when the extensions 15 and 16 are disposed or arranged at an angle A of about 45 degrees relative to the arms 11 and 12 or the plane of movement M of the arms, that this particular angle provides the most satisfactory results for both the positioning of the device 10 relative to the eye and lens L and for removal of the lens from the eye. While angle A is not a conclusive angle, it should be somewhat in the area or extremes of 40 to 50 degrees. These variations still permit some difference in the angular relationship that is induced by the user in holding the device 10 relative to the face and eye when in use. Also, it will be noted that contact with the lens per se by the holders when positioned relative to the eye, is always within the peripheral edge of the lens.

The holders 18 and 19, as noted above, are made of a very soft and pliable, flexible material. It has been found that a very soft and pliable rubber which lends protection to both the lens and the cornea of the eye is most effective as a material from which the holders can be made. On the other hand, other materials having similar properties can also be used with the same results. Various other materials can be used in the construction of the device per se, as well as changes in design or configuration, but, nevertheless, it has been found that the device disclosed and described hereinabove operates very successfully, is easy to handle by the user and can be manufactured in an inexpensive manner.

This invention has been described in detail with particular reference to preferred embodiments thereof but it will be understood that variations and modifications can be effected within the spirit and scope of the invention.

I claim:

1. A device for engaging and removing a plastic contact lens in position relative to the eye of a user, comprising:

a first arm and a second arm having facing surfaces and arranged at an acute angle relative to each other, the arms being integrally joined at one end and formed of a hard, resilient polypropolyene material to establish a first position of maximum separation of the free ends of the arms and being movable, one toward the other and in the same plane, from the first position into a second position of minimum separation of the free ends of the arms;

an extension integral and coextensive with the free end of each of the arms and inclined at an angle of 40-50 degrees relative to its respective arm and the plane of movement of the arms;

means integral with the facing surface of each arm for abutting one another to limit the movement of the arms in the plane of movement to establish the second position of the arms; and a member of generally ellipsoidal shape having a central aperture for receiving a respective extension for mounting one of the same on each arm, each member being provided with a plurality of peripheral, axial grooves with the edge of a corresponding groove on each member releasably engaging the contact lens within the peripheral edge thereof when the arms are in the first position, and slightly folding the contact lens as the arms are moved into the second position, thereby releasing the contact lens from the eye and retaining the same between the members as the device is moved in a direction away from the eye.

2. A device for engaging and removing a plastic contact lens in position relative to the eye of a user in accordance with claim 1 wherein the width of the peripheral, axial grooves vary in width converging in an axial direction from a maximum width at the center of the member to a minimum width at each end thereof.

3. A device for engaging and removing a plastic contact lens in position relative to the eye of a user in accordance with claim 1 wherein the generally ellipsoidal member is of soft rubber.

* * * * *